United States Patent
Uchiyama

(10) Patent No.: US 10,481,061 B2
(45) Date of Patent: Nov. 19, 2019

(54) SENSOR FOR DETECTING AN EMISSION AMOUNT OF PARTICULATE MATTER

(71) Applicant: ISUZU MOTORS LIMITED, Tokyo (JP)

(72) Inventor: Tadashi Uchiyama, Kamakura (JP)

(73) Assignee: ISUZU MOTORS LIMITED, Tokyo (JP)

( * ) Notice: Subject to any disclaimer, the term of this patent is extended or adjusted under 35 U.S.C. 154(b) by 182 days.

(21) Appl. No.: 15/545,213

(22) PCT Filed: Jan. 19, 2016

(86) PCT No.: PCT/JP2016/051481
§ 371 (c)(1),
(2) Date: Jul. 20, 2017

(87) PCT Pub. No.: WO2016/117577
PCT Pub. Date: Jul. 28, 2016

(65) Prior Publication Data
US 2018/0003609 A1 Jan. 4, 2018

(30) Foreign Application Priority Data

Jan. 20, 2015 (JP) .................... 2015-008668
Jan. 13, 2016 (JP) .................... 2016-004641

(51) Int. Cl.
*G01N 15/02* (2006.01)
*G01M 15/10* (2006.01)
(Continued)

(52) U.S. Cl.
CPC .......... *G01N 15/02* (2013.01); *G01M 15/102* (2013.01); *G01N 1/2205* (2013.01);
(Continued)

(58) Field of Classification Search
CPC .... G01N 15/02; G01N 1/2205; G01N 1/2252; G01N 15/0272; G01N 15/0618; G01N 15/0656; G01M 15/102
See application file for complete search history.

(56) References Cited

U.S. PATENT DOCUMENTS 5,021,831 A * 6/1991 Tonomoto .............. B01D 39/14
399/93
5,780,811 A * 7/1998 Kawamura ........ B01D 39/2082
219/202
(Continued)

FOREIGN PATENT DOCUMENTS

GB 2475097 A 5/2011
JP 2002-021537 A 1/2002
(Continued)

OTHER PUBLICATIONS

International Search Report and Written Opinion for PCT App No. PCT/JP2016/051481 dated Apr. 5, 2016, 9 pgs.
(Continued)

*Primary Examiner* — David Z Huang
(74) *Attorney, Agent, or Firm* — Procopio, Cory, Hargreaves & Savitch LLP

(57) ABSTRACT

The sensor includes: a collection part 30L, 30M, 30S in which a plurality of filter members for collecting particulate matter in exhaust gas are arranged in descending order of porosity from an exhaust upstream side to an exhaust downstream side of the exhaust gas; a pair of electrodes 32, 33 which is arranged to each of the plurality of filter members 30L, 30M, 30S and facing each other with the plurality of filter members interposed therebetween; and estimation means 42 to 44 for estimating a particulate matter amount collected on each of the plurality of filter members having different porosities based on a capacitance change amount between the pair of electrodes 32, 33.

16 Claims, 8 Drawing Sheets

(51) Int. Cl.
*G01N 15/06* (2006.01)
*G01N 1/22* (2006.01)
*G01N 15/00* (2006.01)

(52) U.S. Cl.
CPC ....... *G01N 1/2252* (2013.01); *G01N 15/0255* (2013.01); *G01N 15/0272* (2013.01); *G01N 15/0618* (2013.01); *G01N 15/0656* (2013.01); *F01N 2560/05* (2013.01); *G01N 2001/2288* (2013.01); *G01N 2015/0046* (2013.01)

(56) References Cited

U.S. PATENT DOCUMENTS

| | | |
|---|---|---|
| 2008/0048681 A1 | 2/2008 | Birkhofer et al. |
| 2013/0032033 A1* | 2/2013 | Bint .................... G01N 1/2252 96/417 |
| 2013/0298535 A1 | 11/2013 | Aoki |
| 2016/0047732 A1 | 2/2016 | Uchiyama et al. |

FOREIGN PATENT DOCUMENTS

| | | |
|---|---|---|
| JP | 2003-098136 A | 4/2003 |
| JP | 2007-524786 A | 8/2007 |
| JP | 2009-042021 A | 2/2009 |
| JP | 2009-097410 A | 5/2009 |
| JP | 2012-117383 A | 6/2012 |
| JP | 2013-205034 A | 10/2013 |
| JP | 2014159783 A | 9/2014 |
| WO | 2012104994 A1 | 8/2012 |
| WO | 2012160950 A1 | 11/2012 |
| WO | 2014129448 A1 | 8/2014 |

OTHER PUBLICATIONS

Extended European Search Report for related EP App No. 16740184.3 dated Aug. 6, 2018, 20 pgs.

* cited by examiner

SENSOR FOR DETECTING AN EMISSION AMOUNT OF PARTICULATE MATTER

CROSS-REFERENCE TO RELATED APPLICATIONS

This application is a U.S. National Stage entry of PCT Application No. PCT/JP2016/051481, filed on Jan. 19, 2016, which claims priority to Japanese Patent Application Nos. 2015-008668, filed Jan. 20, 2015, and 2016-004641 filed Jan. 13, 2016, the contents of which are incorporated herein by reference.

TECHNICAL FIELD

The present invention relates to a sensor, particularly to a PM sensor which detects emission amount of a particle matter (hereinafter referred to as "PM") contained in exhaust gas m total number for particle sizes (each).

BACKGROUND ART

A sensor is known to detect a particle size distribution and an emission amount of PM contained in exhaust gas discharged from an internal combustion engine. For example, there has been proposed a sensor in which filters having different porosities are arranged in descending order of the porosity from an upstream side of a flow direction of the exhaust gas so as to section a chamber, and which detects a particle size distribution and a PM emission amount based on electromotive force generated by a solid electrolyte layer while burning PM in each particle size, which is collected in the chamber (for example, see Patent Document 1).

PRIOR ART DOCUMENT

Patent Document

Patent Document 1: JP-A-2009-42021

SUMMARY OF THE INVENTION

Problems to be Solved by the Invention

In the sensor described in Patent Document 1, since the electromotive force generated by the solid electrolyte layer is used, during measurement, there is a need to stop the exhaust gas from flowing such that the chamber for collecting the PM becomes an enclosed region. In this sensor, since the exhaust gas is stopped from flowing during measurement, it is not considered to continuously detect the PM amount. In addition, a size of the device is increased, and there are many problems in terms of weight, size, cost, etc. to install the above sensor into automobiles or the like, and thus it is not suitable.

The present invention has been made in view of the above problems, and one object of the present invention is to provide a sensor capable of continuously estimating the PM amount for each particle size of the PM contained in the exhaust gas. Further, the sensor can be mounted in automobiles or the like.

Means for Solving the Problems

A sensor of the disclosure includes: a collection part in which a plurality of filter members, which are for collecting particulate matter in exhaust gas and have different porosities from each other, are arranged in descending, order of the porosity from an exhaust upstream side to an exhaust downstream side of the exhaust gas; a pair of electrodes which is arranged to each of the plurality of filter members and facing each other with the plurality of filter members interposed therebetween; and estimation means for estimating a particulate matter amount collected on each of the plurality of filter members having the different porosities from each other based on a capacitance change amount between the pair of electrodes.

Further, a sensor of the disclosure includes: a collection part in which a plurality of filter members, which are for collecting particulate matter in exhaust gas and have different average pore sizes from each other, are arranged in descending order of the average pore size from an exhaust upstream side to an exhaust downstream side of the exhaust gas; a pair of electrodes which is arranged to each of the plurality of filter members and facing each other with the plurality of filter members interposed therebetween; and estimation means tier estimating a particulate matter amount collected on each of the plurality of filter members having the different average pore sizes from each other based on a capacitance change amount between the pair of electrodes.

Further, a sensor of the disclosure includes: a collection part in which a plurality of filter members, which are for collecting particulate matter in exhaust gas and have different physical properties from each other, are arranged in descending order of the physical property from an exhaust upstream side to an exhaust downstream side of the exhaust gas; a pair of electrodes which are arranged to each of the plurality of filter members and facing each other with the plurality of filter members interposed therebetween; and a control unit, wherein the physical property is a porosity or an average pore size; and wherein the control unit operates to execute the following processing; estimation processing for estimating a particulate matter amount collected on each of the plurality of filter members having the different physical properties based on a capacitance change amount between the pair of electrodes.

Effect of the Invention

According to the present invention, it is possible to continuously estimate the PM amount for each particle size of the PM contained in the exhaust gas.

Figure 7:
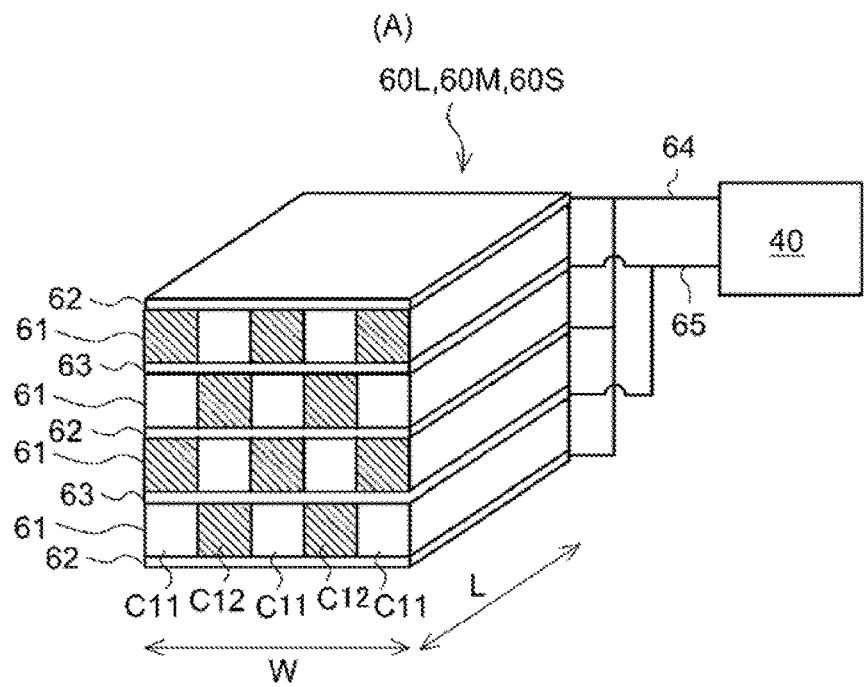
Figure 7:
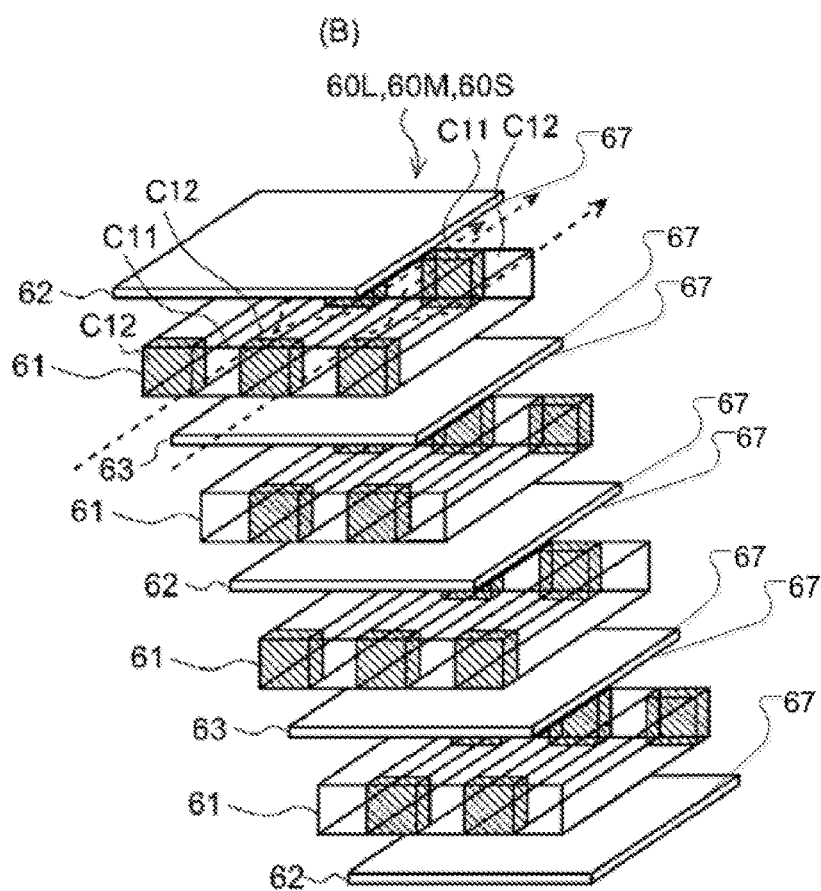

(A) of FIG. 7 is a schematic perspective view of each PM sensor part according to the third embodiment, and (B) of FIG. 7 is a schematic exploded perspective view of each PM sensor part according to the third embodiment.

Figure 8:
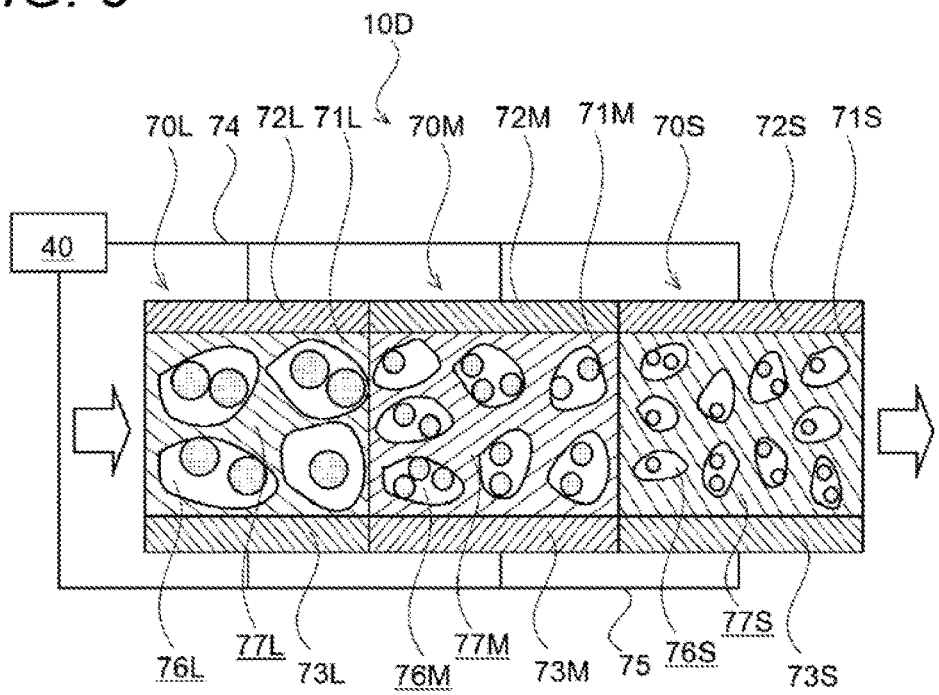

FIG. 8 is a schematic sectional view showing a PM sensor according to a fourth embodiment.

Figure 9:
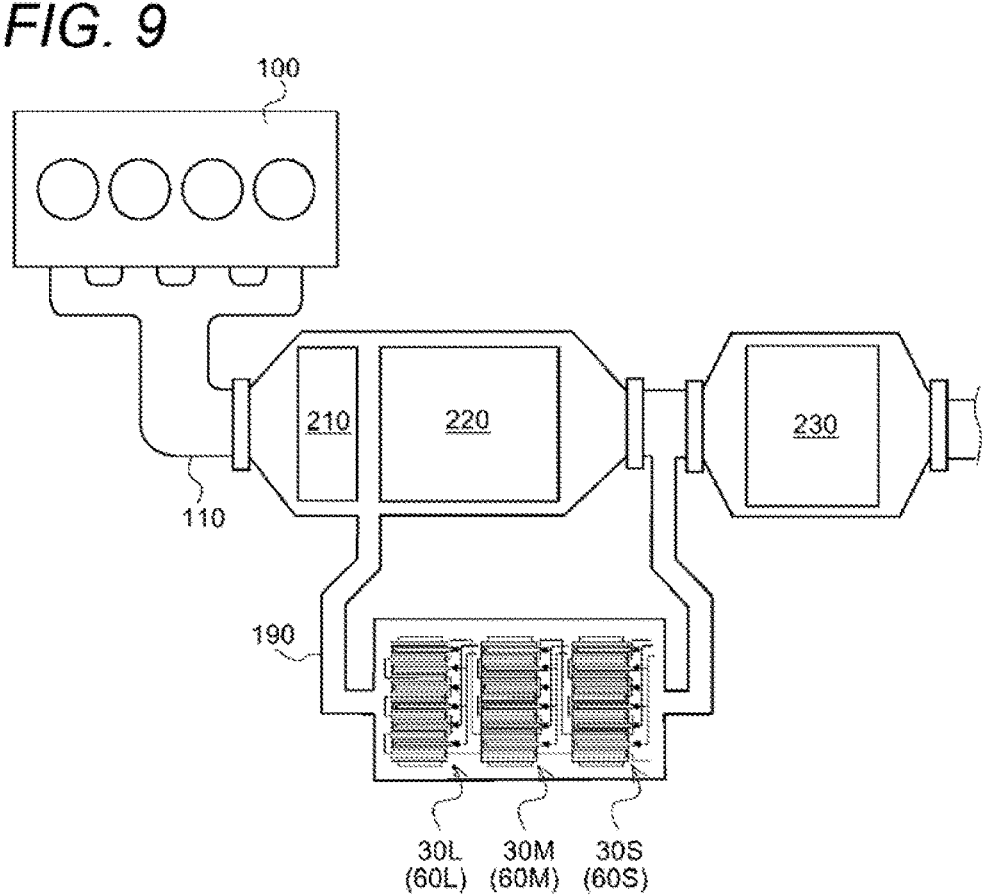

FIG. 9 is a schematic configuration diagram showing an example of an exhaust system to which a PM sensor is applied, according to another embodiment.

MODE FOR CARRYING OUT THE INVENTION

A sensor according to each embodiment of the present invention will be described with reference to appended drawings. Same components are given same reference numerals, and their names and functions are same as well. Therefore, detailed descriptions of such components are not repeated.

First Embodiment

Figure 1:
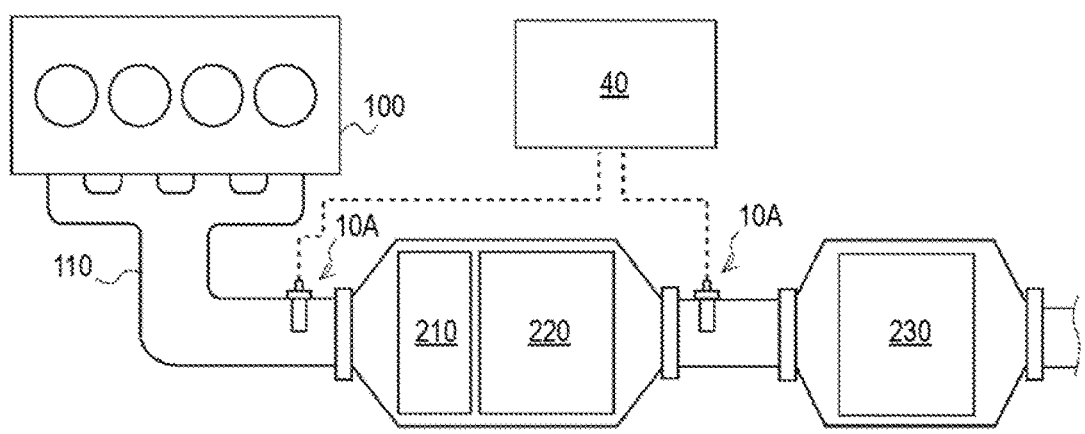
FIG. 1 is a schematic configuration diagram showing an example of an exhaust system to which a PM sensor according to a first embodiment is applied.

FIG. 1 is a schematic configuration diagram showing an example of an exhaust system of a diesel engine (hereinafter referred to as "engine") 100 to which a sensor 10A according to a first embodiment is applied. An oxidation catalyst 210, a diesel particulate filter (DPF) 220, and a NOx purification catalyst 230 are sequentially provided in an exhaust pipe 110 of the engine 100 from an exhaust upstream side. The sensor 10A according to this embodiment is preferably provided at a downstream side of the DPF 220 in the exhaust pipe 110. The sensor 10A may be provided at an upstream side of the oxidation catalyst 210 in the ex crust pipe 110.

The detailed configuration of the sensor 10A according to this embodiment will be described with reference to FIG. 2.

The sensor 10A includes a case member 11 which is inserted in the exhaust pipe 110, a pedestal 20 through which the case member 11 is installed into the exhaust pipe 110, a first sensor part 30L, a second sensor part 30M, and a third sensor part 30S which are accommodated in the case member 11, and a control unit 40.

The case member 11 is a cylinder with a closed bottom side (the lower side in the figure). A length L of the case member 11 in an axial direction of the cylinder is substantially equal to a radius R of the exhaust pipe 110, such that a cylinder wall portion at the bottom side protrudes approximately to a center line CL of the exhaust pipe 110. In the following description, the bottom side of the case member 11 is described as a top-end side and the side opposite to the bottom side is described as a base-end side.

A plurality of inlets 12 are spaced at intervals in a circumferential direction an the cylinder wall portion at the top-end side of the case member 11. A plurality of outlets 13 are spaced at intervals along a circumferential direction on the cylinder wall portion at the base-end side of the case member 11. A total opening area S12 of the inlets 12 is less than a total opening area S13 of the outlets 13 (S12<S13). That is, since exhaust flow velocity V12 near the inlets 12 is less than exhaust flow velocity V13 near the outlets 13 (V12<V13), a pressure P12 at the inlets 12 is higher than a pressure P13 at the outlets 13 (P12>P13). Therefore, exhaust gas flows into the case member 11 smoothly from the inlets 12, while the exhaust gas in the case member 11 flows into the exhaust pipe 110 smoothly from the outlets 13.

The pedestal 20 includes a male-thread part 21 and a nut part 22. The male-thread part 21 at the base end of the case member 11 closes the opening of the case member 11 at the base-end side. The male-thread part 21 is screwed with a female-thread part of a boss 110A formed in the exhaust pipe 110. The nut part 22 is, for example, a hexagon nut and is fixed to an upper end of the male-thread part 21. Penetration holes (not shown), through which conductive wires 34L, 34M, 34S, 35L, 35M, 35S or the like described later are inserted, are formed to the male-thread part 21 and the nut pan 22.

The first sensor part 30L includes a first filter member 31L and a plurality of pairs of first electrodes 32L, 33L.

The first filter member 31L configures a part of a collection pan of the present invention, and is formed by alternately sealing upstream and downstream sides of a plurality of cells which form a grid-like exhaust how path sectioned by porous ceramic partition walls. In a state where a direction of the flow path of the cells is substantially parallel to the axial direction (upper-lower direction in the figure) of the case member 11, the first filter member 31L is held on an inner circumferential surface of the case member 11 through a cushion member $CM_L$. PM in the exhaust gas flowing into the case member 11 from the inlets 12 is collected on partition wall surfaces or pores by making the exhaust gas flow into the cells with sealed upstream sides $C2_L$ from the cells with sealed downstream sides $C1_L$, as shown by a dashed arrow in FIG. 3. In the following description, the cells with sealed upstream sides will be described as first cells for measurement $C1_L$, and the cells with sealed downstream sides will be described as first cells for electrode $C2_L$.

The first electrodes 32L, 33L are, for example, conductive metal wires, and are alternately inserted into the cells for electrode $C2_L$, which face each other with the cell for measurement $C1_L$ interposed therebetween, from the downstream side (unsealed side) to form a capacitor. The first electrodes 32L, 33L are respectively connected to a capacitance detection circuit, which is not shown and built in the control unit 40, through the first conductive wires 34L, 35L.

Figure 2:
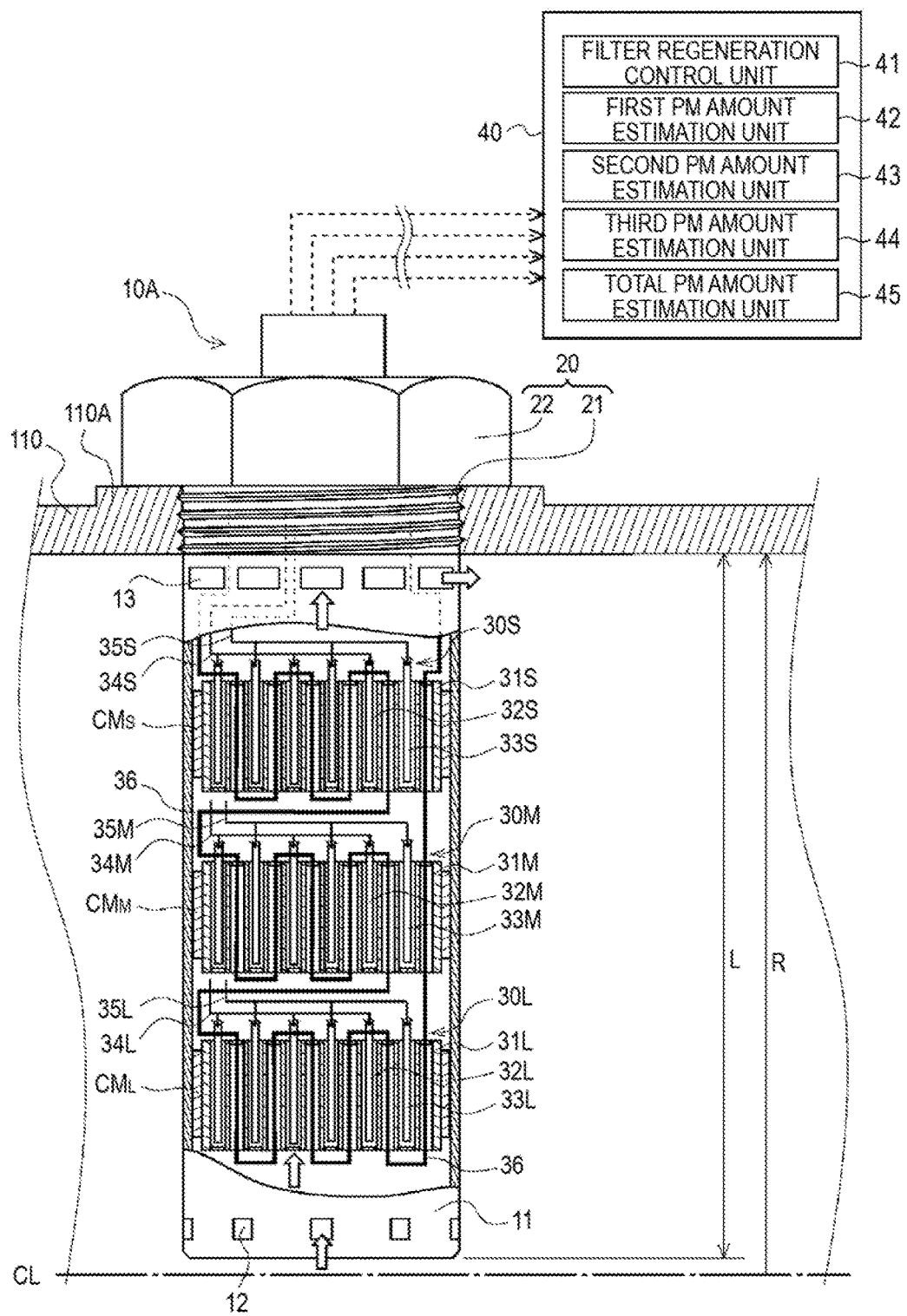
FIG. 2 is a schematic partial sectional view showing the PM sensor according to the first embodiment.

As shown in FIG. 2, the second sensor part 30M includes a second filter member 31M and a plurality of pairs of second electrodes 32M, 33M.

The second filter member 31M configures a part of a collection part of the present invention, and is arranged at a downstream side of the first filter member 31L in the flow path of the exhaust gas. The second filter member 31M is held on the inner circumferential surface of the case member 11 through a cushion member $CM_M$. The second filter member 31M has a porosity (or average pore size) smaller than that of the first filter member 31L. That is, the second filter member 31M is provided with pores having diameters smaller than those of the first filter member 31L, as to collect the in the exhaust gas which is not collected by the first filter member 31L.

Figure 3:
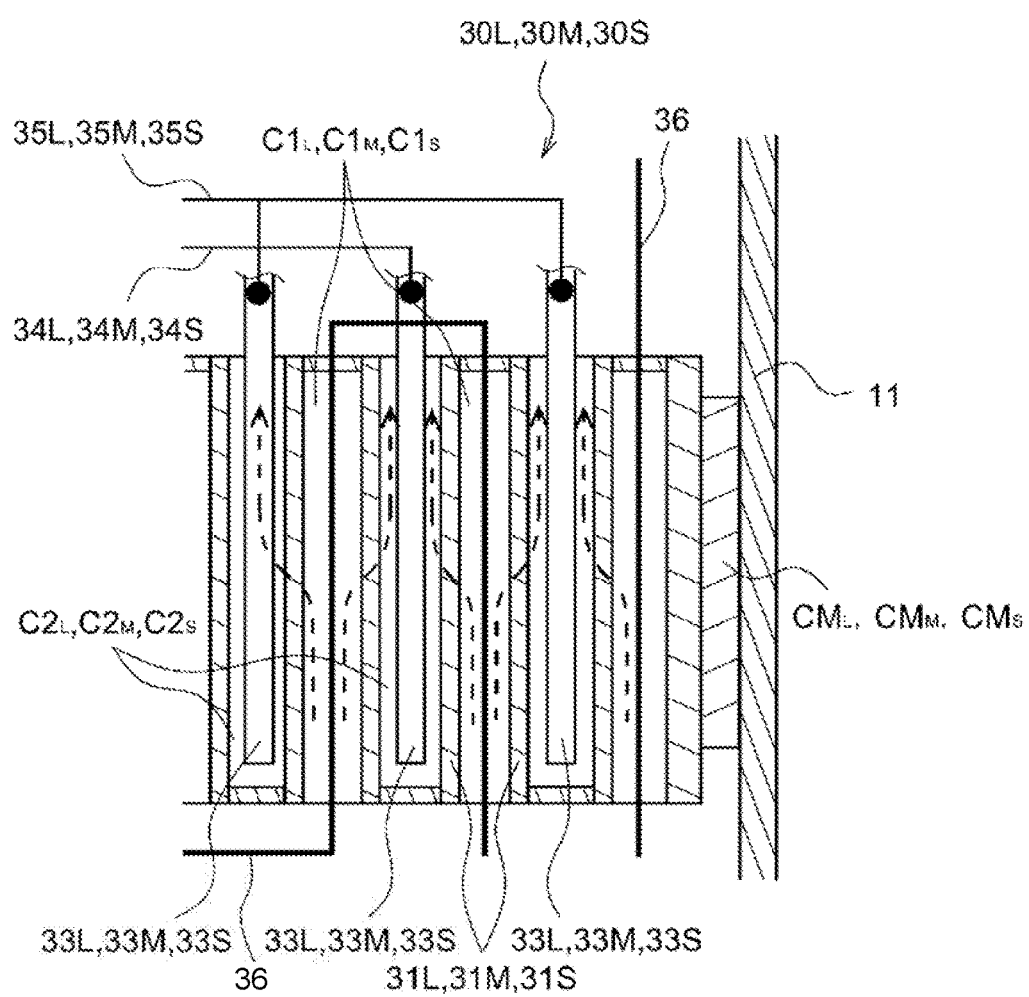
FIG. 3 is a partial enlarged sectional view showing main parts of the PM sensor according to the first embodiment.

As shown in FIG. 3, the second filter member 31M has cells with sealed downstream sides $C1_M$ and cells with sealed upstream sides $C2_M$, as the first filter member 31L does. The second electrodes 32M, 33M are, for example, conductive metal wires, and are alternately inserted into the cells for electrode $C2_M$ opposite from the downstream side (unsealed side) to form a capacitor with the cell for measurement $C1_M$ interposed therebetween. The second electrodes 32M, 33M are respectively connected to the capacitance detection circuit through the second conductive wires 34M, 35M.

As shown in FIG. 2, the third sensor part 30S includes a third filter member 31S and a plurality of pairs of third electrodes 32S, 33S.

The third filter member 31S is part of a collection part of the present invention, and is arranged at a downstream side of the second filter member 31M in the flow path of the exhaust gas. The third filter member 31S is held on the inner circumferential surface of the case member 11 through a cushion member $CM_S$.

The third filter member 31S has a porosity (or average pore size) smaller than that of the second filter member 31M. That is, the third filter member 31S is provided with pores having diameters smaller than those of the second filter member 31M, so as to collect the PM in the exhaust gas which is not collected by the second filter member 31M.

As shown in FIG. 3, the third filter member 31S has cells with sealed downstream sides $C1_S$ and cells with sealed upstream sides $C2_S$, as the first filter member 31L and the second filter member 31M do.

The third electrodes 34S, 35S are, for example, conductive metal wires, and are alternately inserted into the cells for electrode $C2_S$, which face each other with the cell for measurement $C1_S$ interposed therebetween, from the downstream side (unsealed side) to form a capacitor. The third electrodes 32S, 33S are respectively connected to the capacitance detection circuit through the third conductive wires 34S, 35S.

As shown in FIG. 2, an electric heater 36 is provided with respect to each of the sensor parts 30L, 30M, 30S. The electric heater 36 is, for example, a heating wire, and configures regeneration means of the present invention. The electric heater 36 performs a so-called filter regeneration (hereinafter referred to as "sensor regeneration"), in which the PM accumulated on the cells for measurement is burnt and removed, by being energized to heat the cells for measurement $C1_L$, $C1_M$, $C1_S$ respectively included in the sensor parts 30L, 30M, 30S. As at result, the electric heater 36 is bent into a continuous S shape at each of the filter members 31L, 31M, 31S, and has its parallel line parts inserted into each of the cells for measurement $C1_L$, $C1_M$, $C1_S$ along the how path. Since the electric heater 36 according to this embodiment arranges a series of heating wires in a state of surrounding each of the sensor parts 30L, 30M, 30S, the sensor parts 30L, 30M, 30S are heated collectively.

The control unit 40 performs various controls and includes a CPU, a ROM, a RAM, an input port, an output port, etc. which are well known. Further, the control unit 40 includes a filter regeneration control unit 41, a first PM amount estimation unit 42, a second PM amount estimation unit 43, a third PM amount estimation unit 44, and a total PM amount estimation unit 45 as functional elements. Although the functional elements are described as being contained in the control unit 40, which is integrated hardware, they may be provided in separated hardware.

The filter regeneration control unit 41, which is au example of the regeneration means of the present invention, performs control of the sensor regeneration in which the electric heater 36 is turned on (energized) based on capacitance $Cp_L$, $Cp_M$, $Cp_S$ between each of the electrodes 33L, 33M, 33S and each of the pairing electrodes 32L, 32M, 32S detected by the capacitance detection circuit (not shown).

The capacitance $Cp_L$ between the first electrodes 32L, 33L, dielectric constant $\varepsilon_L$ of a medium between the first electrodes 32L, 33L, a surface area $S_L$ of the first electrodes 32L, 33L, and distance $d_L$ between the first electrodes 32L, 33L have a relationship represented by the following Equation (1).

[Equation 1]

$$Cp_L = \sum \left( \varepsilon_L \times \frac{S_L}{d_L} \right) \quad (1)$$

In Equation (1), the surface area $S_L$ of the first electrodes 32L, 33L is constant. When the PM is collected on the cells for measurement $C1_L$, the dielectric constant $\varepsilon_L$ and, the distance $d_L$ change, and the capacitance $Cp_L$ changes accordingly. That is, a proportional relationship is established between the capacitance $Cp_L$ between the first electrodes 32L, 33L and a PM accumulation amount on the first filter member 31L.

The capacitance $Cp_M$ between the second electrodes 12M, 33M, dielectric constant $\varepsilon_M$ of a medium between the second electrodes 32M, 33M, a surface area $S_M$ of the second, electrodes 32M, 33M, and distance $d_M$ between the second electrodes 32M, 33M have a relationship represented by the following Equation (2),

[Equation 2]

$$Cp_M = \sum \left( \varepsilon_M \times \frac{S_M}{d_M} \right) \quad (2)$$

In Equation (2), the surface area $S_M$ of the second electrodes 32M, 33M is constant. When the PM is collected on the cells for measurement $C1_M$, the dielectric constant $\varepsilon_M$ and the distance $d_M$ change, and the capacitance $Cp_M$ changes accordingly. As a result, a proportional relationship is established between the capacitance $Cp_M$ between the second electrodes 32M, 33M and a PM accumulation amount on the second member 31M, similar to the first electrodes 32L, 33L.

The capacitance $Cp_S$ between the third electrodes 32S, 33S, dielectric constant $\varepsilon_S$ of a medium between the third electrodes 32S, 33S, a surface area $S_S$ of the third electrodes 32S, 33S, and distance $d_S$ between the third electrodes 32S, 33S have a relationship represented by the following Equation (3).

[Equation 3]

$$Cp_S = \sum \left( \varepsilon_S \times \frac{S_S}{d_S} \right) \quad (3)$$

In Equation (3), the surface area $S_S$ of the third electrodes 32S, 33S is constant. When the PM is collected on the cells for measurement C1S, the dielectric constant $\varepsilon_S$ and the distance $d_S$ change, and the capacitance $Cp_M$ changes accordingly. As a result, a proportional relationship is established between the capacitance $Cp_S$ between the third electrodes 32S, 33S and a PM accumulation amount on the third member 31S, similar to the first electrodes 32L, 33L.

In this embodiment, the first PM amount estimation unit 42, the second PM amount estimation unit 43, and the third PM amount estimation unit 44 estimate a PM amount accumulated on each of the filter members 31L, 31M, 31S.

The first PM amount estimation unit 42, which is an example of estimation means of the present invention, estimates and calculates a PM amount collected on the first filter member 31L during a regeneration interval period, which is from an end of a filter regeneration to a start of a next filter regeneration, based on a capacitance change amount $\Delta Cp_L$ between the first electrodes 32L, 33L.

The second PM amount estimation unit 43, which is an example of the estimation means of the present invention, estimates and calculates a PM amount collected on the second filter member 31M during a regeneration interval period, which is from au end of a filter regeneration to a start of a next filter regeneration, based on a capacitance change amount $\Delta Cp_M$ between the second electrodes 32M, 33M.

The third PM amount estimation unit 44, which is an example of the estimation means of the present invention, estimates and calculates a PM amount collected on the third filter member 31S during a regeneration interval period, which is from an end of a filter regeneration to a start of a next filter regeneration, based on a capacitance change amount $\Delta Cp_S$ between the third electrodes 32S, 33S.

More specifically, the PM amount estimation units 43 to 44 calculate sequentially PM amounts $m_{PM\_Int\_L}$, $m_{PM\_Int\_M}$, $m_{PM\_Int\_S}$ during interval periods respectively, based on the following Equations (4) to (6). In Equations (4) to (6), the capacitance change amounts $\Delta Cp_L$, $\Delta Cp_M$, $\Delta Cp_S$ respectively between the electrodes 32L, 32M, 32S and the pairing electrodes 33L, 33M, 33S is multiplied by a first order coefficient $\beta$.

[Equation 4]

$$m_{PM\_Int\_L} = \beta \cdot \Delta Cp_L \quad (4)$$

$$m_{PM\_Int\_M} = \beta \cdot \Delta Cp_M \quad (5)$$

$$m_{PM\_Int\_S} = \beta \cdot \Delta Cp_S \quad (6)$$

Figure 4:
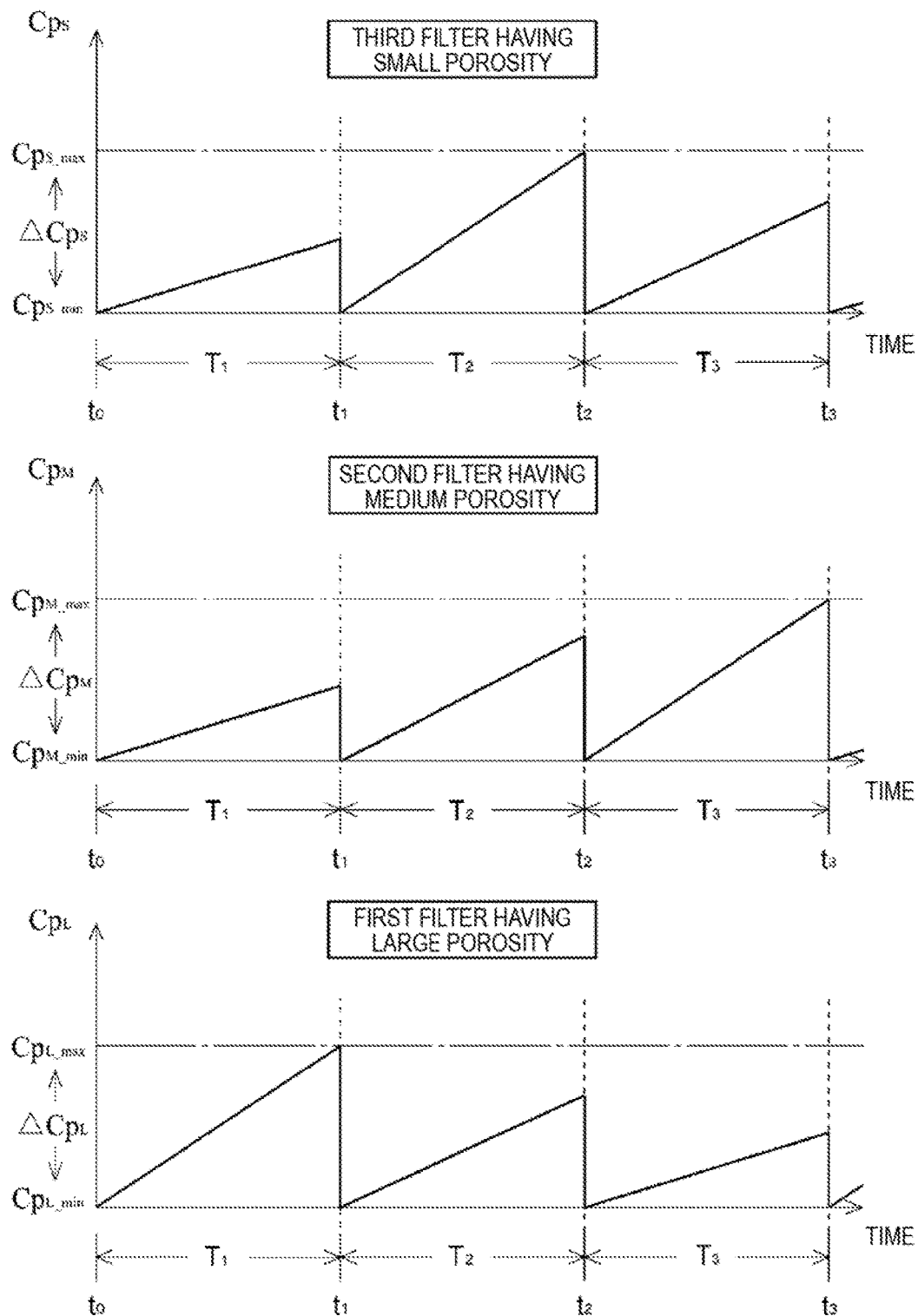
FIG. 4 is a timing chart illustrating filter regeneration, change in a temperature of a filter, and integration of a PM amount.

As shown in FIG. 4, the filter regeneration control unit 41 turns on the electric heater 36 to start the filter regeneration when any of the capacitance $Cp_L$ between the first electrodes 32L, 33L included in the first filter member 31L, the capacitance $Cp_M$ between the second electrodes 32M, 33M included in the second filter member 31L, and the capacitance $Cp_S$ between the third electrodes 32S, 33S included in the third filter member reaches predetermined capacitance maximum thresholds $Cp_{L\_max}$, $Cp_{M\_max}$, $Cp_{S\_max}$ indicating a maximum PM accumulation amount. The filter regeneration is performed on all of the filter members 30L, 30M, 30S until capacitance of target electrodes decrease to predetermined capacitance minimum thresholds $Cp_{L\_min}$, $Cp_{M\_min}$, $Cp_{S\_min}$ indicating a complete removal of PM.

In the example shown in FIG. 4, since the capacitance $Cp_L$ of the first filter member 31L during a first interval period $T_1$, which is from a filter regeneration time $t_0$ to a filter regeneration time $t_1$, has reached the capacitance maximum threshold $Cp_{L\_max}$, the filter regeneration is performed on each of the filter members 31L, 31M, 31S.

Similarly, since the capacitance $Cp_S$ of the third filter member 31S during a second interval period $T_2$, which is from the filter regeneration time $t_1$ to a filter regeneration time $t_2$, has reached the capacitance maximum threshold $Cp_{S\_max}$, and the capacitance $Cp_M$ of the second filter member 31M during a third interval period $T_3$, which is from the filter regeneration time $t_2$ to a filter regeneration time $t_3$, has reached the capacitance maximum threshold $Cp_{M\_max}$, the filter regeneration is performed on each of the filter members 31L, 31M, 31S.

The total PM amount estimation unit 45 estimates a PM amount accumulated on the whole sensor 10A. As a result, the total PM amount estimation unit 45 receives in real time and adds up estimated values from the first. PM amount estimation unit 42, the second PM amount estimation unit 43, and the third PM amount estimation unit 44, so as to obtain a total estimated value of the PM amount.

In this way, the sensor 10A according to this embodiment make it possible to estimate the PM amount in the exhaust gas discharged from the engine 100 in real time and with high accuracy, by calculating interval PM amounts $m_{PM\_Int\_L}$, $m_{PM\_Int\_M}$, $m_{PM\_Int\_S}$ based on the capacitance change amounts $\Delta Cp_L$, $\Delta Cp_M$, $\Delta Cp_S$ during a regeneration interval period $T_n$.

Further, the sensor 10A includes the sensor parts 30L, 30M, 30S which include the three filter members 31L, 31M, 31S with different pore sizes, respectively. Besides, the sensor parts 30L, 30M, 30S are arranged such that a Filter member with a smaller porosity and pore size is at a downstream side of a filter member with a larger porosity and pore size in the flow direction of the exhaust gas. In this way, the PM in the exhaust gas can be accumulated on each of the filter members 31L, 31M, 31S in a state of being separated according to each particle size, and a PM amount in each particle size can be estimated in real time and with high accuracy.

Further, since the electric heater 36 is continuously arranged in the state of surrounding each of the filter members 31L, 31M, 31S, a shortcoming that PM accumulated on one filter member is burnt out by a regeneration process in another filter member can be suppressed. In this way, the PM amount in each particle size can be estimated with higher accuracy.

Further, in the PM sensor 10A according to this embodiment, the top-end portion of the case member 11 accommodating the sensor part 30 protrudes approximately to the center line CL where the exhaust velocity is the greatest in the exhaust pipe 110. The inlets 12, through which the exhaust gas flows into the case member 11, are provided at the cylinder wall portion at the base-end side of the case member 11. In addition, the outlets 13, whose opening area is larger than that of the inlets 12, are provided at the cylinder wall portion at the base-end side of the case member 11. That is, according to the PM sensor 10 in this embodiment, a large difference in a static pressure between the inlets 12 and the outlets 13 can be ensured by arranging the inlets 12 approximately to the center line CL where the exhaust velocity is the greatest in the exhaust passage 110, and enlarging the opening area of the outlets 13, thereby facilitating the flow of the exhaust gas through the sensor part 30.

The PM sensor 10 according to this embodiment is configured to reliably collect the PM in the exhaust gas by each of the filter members 31L, 31M, 31S. Thus, according to the PM sensor 10, the estimation accuracy of the PM amount can be effectively ensured even in an operation state where a flow amount of the exhaust gas increases.

Second Embodiment

Figure 5:
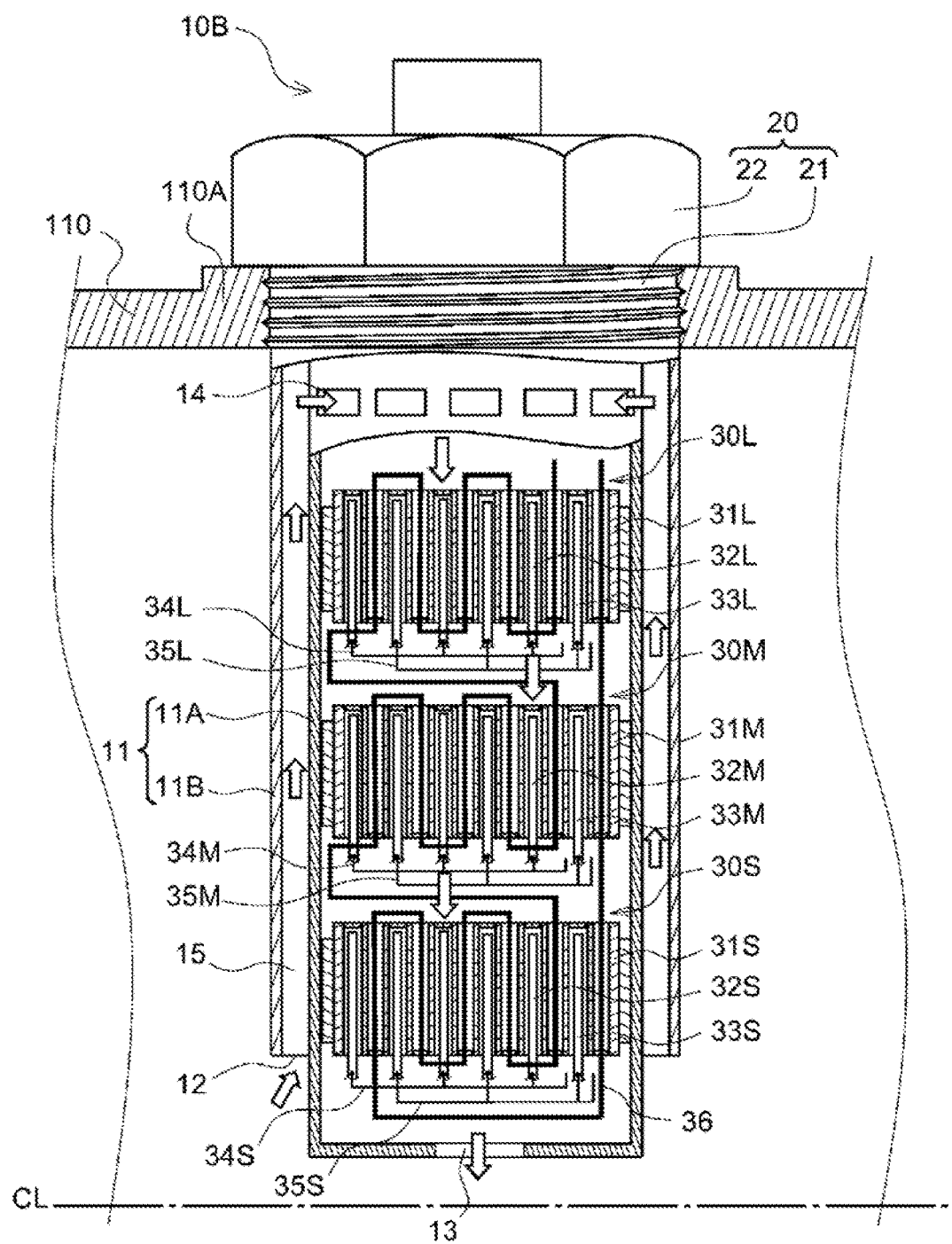
FIG. 5 is a schematic partial sectional view showing a PM sensor according to a second embodiment.

Next, details of a PM sensor 10B according to a second embodiment will be described with reference to FIG. 5. The PM sensor 10B according to the second embodiment is a sensor whose case member 11 has a double tube structure on the basis of the PM sensor 10A according to the first embodiment. Since other components are the same, the detailed description thereof will be omitted. In addition, drawings of some components such as the control unit 40 are omitted.

The case member 11 according to the second embodiment includes a bottomed cylinder inner case member 11A and a cylinder outer case member 11B surrounding a cylinder outer circumferential surface of the inner case member 11A.

The inner case member 11A has an axial length longer than that of the outer case member 11B, such that a top-end side thereof protrudes further than the outer case member 11B. Outlets 13 for introducing exhaust gas in the inner case member 11A into an exhaust pipe 110 are provided in the bottom of the inner case member 11A. Further, a plurality of passage ports 14 are spaced at intervals in a circumferential direction at a cylinder wall portion at the base-end side of the inner case member 11A. The passage ports 14 make the exhaust gas in a flowing path 15 sectioned by the outer circumferential surface of the inner case member 11A and an inner circumferential surface of the outer case member 11B flow through the inner case member 11A.

Annular inlets 12, which are sectioned by a cylinder wall portion at the top-end side of the inner case member 11A and a top end of the outer case member 11B, are formed to a downstream end of the flowing path 15. An opening area S12 of the inlets 12 is less than an opening area S13 of the outlets 13 (S12<S13).

That is, the exhaust gas flowing through the exhaust pipe 110 contacts the cylinder wall surface of the inner case member 11A which protrudes to the top-end side further than the outer case member 11B, and flows into the flowing path 15 from the inlets 12 arranged near a center line CL of the exhaust pipe 110 smoothly. Further, the exhaust gas flowing in the flowing path 15 flows into the inner case member 11A, flows through a filter member 31, and flows into the exhaust pipe 110 from the outlets 13 arranged near the center line CL of the exhaust pipe 110 smoothly. In this way, in the PM sensor 10B according to the second embodiment, an exhaust flow amount flowing through the filter member 31 can be effectively increased by arranging the inlets 12 and the outlets 13 near the center line CL at which exhaust flow velocity is the greatest in the exhaust pipe 110.

Third Embodiment

Figure 6:
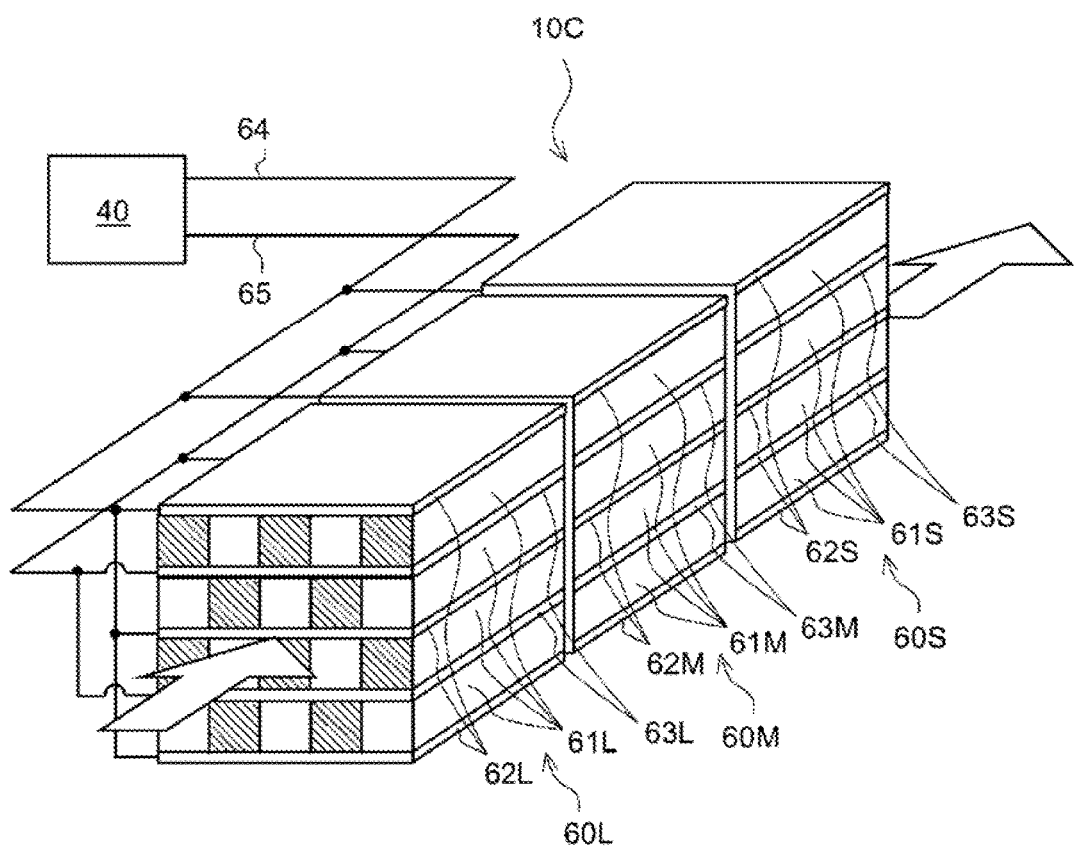
FIG. 6 is a schematic perspective view of a PM sensor according to a third embodiment.

Next, details of a sensor 10C according to a third embodiment will be described. As shown in FIG. 6, the sensor 10C according to the third embodiment is a sensor in which the sensor parts 30L, 30M, 30S according to the first embodiment are formed as laminated sensor parts 60L, 60M, 60S.

Herein, a difference among the sensor parts 60L, 60M, 60S is a difference in porosity of each of filter layers 61L, 61M, 61S. Thus, each of the filter layers 61L, 61M, 61S has same appearance. In addition, first electrode plates 62L, 62M, 62S and second electrode plates 63L, 63M, 63S are same members.

Thus, in the following description, each of the filter layers 61L, 61M, 61S is described as a filter layer 61, each of the first electrode plates 62L, 62M, 62S is described as a first electrode plate 62, and each of the second electrode plates 63L, 63M, 63S is described as a second electrode plate 63. Similarly, conductive wires 64L, 64M, 64S and pairing conductive wires 65L, 65M, 65S are described as conductive wires 64, 65. Since other components in addition to the sensor parts 60L, 60M, 60S have the same structure, the detailed description and drawings thereof are omitted.

(A) of FIG. 7 is a perspective view of the sensor parts 60L, 60M, 60S included in the sensor 10C, and (B) of FIG. 7 shows an exploded perspective view of the sensor parts 60L, 60M, 60S.

The sensor parts 60L, 60M, 60S include a plurality of filter layers 61, a plurality of first and second electrode plates 62, 63, and the conductive wires 64, 65.

The filter layers 61 are, for example, formed by alternately sealing upstream and downstream sides of a plurality of cells which form an exhaust flow path sectioned by porous ceramic partition walls, and formed as cuboids in which the plurality of cells are arranged in parallel in one direction. As shown by the dashed arrow in (B) of FIG. 7, PM contained in exhaust gas is collected on partition wall surfaces or pores of cells C11 by making the exhaust gas flow into cells C12 with sealed upstream sides from the cells C11 with sealed downstream sides. In the following description, a length direction (arrow L in (A) of FIG. 7) of the sensor parts 60L, 60M, 60S is taken as a cell flow path direction, and a width direction (arrow W in (A) of FIG. 7) of the sensor parts 60L, 60M, 60S is taken as a direction perpendicular to the cell flow path direction.

The first and second electrode plates 62, 63 are, for example, flat conductive members, and have a length L and a width W substantially equal to those of the filter layers 61. The first and second electrode plates 62, 63 are stacked alternately with the filter layer 61 interposed therebetween, and are connected to a capacitance detection circuit, which is not shown and built in a control unit 40, through the conductive wires 64, 65 respectively.

That is, the cells C11 are integrally formed as a capacitor, by arranging the first electrode plate 62 and the second electrode plate 63 to face each other with the filter layer 61 interposed therebetween. In this way, in the sensor 10C according to the third embodiment, an electrode surface area S can be effectively ensured and an absolute value of the detectable capacitance can be increased by making the cells C11 integrally form a capacitor by the flat electrode plates 62, 63. In addition, since the distance d between the electrodes is the cell pitch and is uniformed, variation of initial capacitance can be effectively suppressed.

Voltage may be applied to the electrode plates 62, 63 directly, or a heater substrate 67 or the like not shown may be provided between the filter layer 61 and the electrode plates 62, 63, when burning and removing the PM accumulated on the cells C11.

Fourth Embodiment

Next, details of a sensor 10D according to a fourth embodiment will be described. As shown in FIG. 8, the sensor 10D according to the fourth embodiment is a sensor in which the sensor parts 30L, 30M, 30S according to the first embodiment are formed as sensor parts 70L, 70M, 70S made of ceramics with different porosities and average pore sizes.

FIG. 8 shows a sectional view of an exhaust flow direction of the sensor parts 70L, 70M, 70S included in the sensor 10D.

The sensor parts 70L, 70M, 70S include filter layers 71L, 71M, 71S, first electrode plates 72L, 72M, 72S, second electrode plates 73L, 73M, 73S, and conductive wires 74, 75, respectively.

The filter layers 71L, 71M, 71S are made of porous ceramics, and have a plurality of pores 76L, 76M, 76S for collecting PM and wall portions 77L, 77M, 77S for forming the pores 76L, 76M, 76S respectively.

A porosity of a filter layer 71L is larger than that of a filter layer 71M and a filter layer 71S. Further, an average pore size obtained by averaging pore sizes of the pores 76L of the filter layer 71L is larger than those of other filter layers 71M, 71S. That is, in the this embodiment, the filter layers 71L, 71M, 71S are arranged in descending order of porosity (or average pore size) from an exhaust upstream side to an exhaust downstream side of the exhaust gas.

The PM contained in the exhaust gas flowing into the sensor parts 70L, 70M, 70S flows into the pores 76L, 76M, 76S which are formed by being sectioned by the wall portions 77L, 77M, 77S. The PM with a diameter larger than those of the pores 76L, 76M, 76S of the sensor parts 70L, 70M, 70S is collected in the pores 76L, 76M, 76S, the PM with a diameter smaller than those of the pores 76L, 76M, 76S of the sensor parts 70L, 70M, 70S passes through the pores 76L, 76M, 76S and flows to a downstream side of the filter layers 71L, 71M, 71S. In this way, the PM with a diameter larger than the pore size corresponding to the porosity of each of the filter layers 71L, 71M, 71S, which are arranged in descending order of porosity (or the average pore size) from the exhaust upstream side of the exhaust gas, is collected on the filter layers 71L, 71M, 71S of the sensor parts 70L, 70M, 70S respectively.

The first electrode plates 72L, 72M, 72S and the second electrode plates 73L, 73M, 73S are, for example, flat conductive members, and external dimensions thereof are substantially similar to those of the filter layers 71L, 71M, 71S. The first electrode plates 72L, 72M, 72S and the second electrode plates 73L, 73M, 73S are arranged to interpose the filter layers 71L, 71M, 71S therebetween, and are connected to a capacitance detection circuit, which is not shown and built in a control unit 40, through the conductive wires 74, 75 respectively.

That is, the pores 76L, 76M, 76S forms a capacitor in entire, by arranging the first electrode plates 72L, 72M, 72S and the second electrode plates 73L, 73M, 73S to face each other with the filter layers 71L, 71M, 71S interposed therebetween.

Voltage may be applied to the first electrode plates 72L, 72M, 72S and the second electrode plates 73L, 73M, 73S directly, or a heater substrate or the like not shown may be provided between the filter layers 71L, 71M, 71S and the first electrode plates 72L, 72M, 72S and the second electrode plates 73L, 73M, 73S, when burning and removing the PM accumulated on the pores 76L, 76M, 76S.

Although the filter layers 71L, 71M, 71S according to this embodiment are preferably formed of cordierite ceramics, as long as it a member having heat resistance, capable of passing exhaust gas, and capable of knowing the porosity, they can be suitably used as a member constituting the filter layers.

[Others]

The present invention is not limited to the above embodiments, but can be appropriately modified and implemented without departing from the spirit of the present invention.

For example, as shown in FIG. 9, a bypass pipe 190 branching from between the oxidation catalyst 210 and the DPF 220 and joining at an upstream side of the NOx purification catalyst 230 may be connected to the exhaust pipe 110, and the sensor parts 30L, 30M, 30S according to the first embodiment or the sensor parts 60L, 60M, 60S according to the third embodiment may be arranged in the bypass pipe 190.

Further, in the above embodiments, the plurality of sensor parts 30L, 30M, 30S are heated collectively using the single electric heater 36. However, electric heaters may be separately provided in each of the sensor parts 30L, 30M, 30S for regeneration control. In this case, it is preferable to collectively perform the regeneration process on a sensor part to be regenerated and a sensor part at the downstream side of the exhaust gas flow direction from this sensor part. That is, when the particulate matter amount accumulated on the cells of one filter member is equal to or greater than a predetermined amount, filter regeneration is performed, i.e., a plurality of filter members including the filter member and a filter member adjacent to the filter member at the downstream side are heated to burn and remove the particulate matter. This is because the PM accumulated at the downstream side may be burnt out by the heated exhaust gas generated during the regeneration process of the sensor part at the upstream side.

Further, in the above embodiments, three types of filter members 31L, 31M, 31S with different pore sizes are provided, but the number of types of the filter members is not limited thereto. Two or more types of the filter members may be provided.

In the first embodiment (or the second embodiment), although not shown, positions of the inlets 12 and the outlets 13 may be reversed and the exhaust gas may flow into the case member 11 in a reverse direction. In this case, the filter members 31L, 31M, 31S may be accommodated reversely in the case member 11.

This application is based on Japanese Patent Application No. 2015-008668 filed on Jan. 20, 2015 and Japanese Patent Application No. 2016-004641 filed on Jan. 13, 2016, contents of which are incorporated herein by reference.

INDUSTRIAL APPLICABILITY

The sensor of the present invention is useful in that it can continuously estimate the PM amount in each particle size of the PM contained in the exhaust gas.

REFERENCE SIGNS LIST 10A, 10B, 10C, 10D sensor
11 case member
12 inlet
13 outlet
20 pedestal
21 male-thread part
22 nut part
30L first sensor part
30M second sensor part
30S third sensor part
31L first filter member (collection part)
31M second filter member (collection part)
31S third filter member (collection part)
32L, 33L first electrode
32L, 33M second electrode
32S, 33S third electrode
36 electric heater (regeneration means)
40 control unit
41 filter regeneration control unit (regeneration means)
42 first PM amount estimation unit (estimation means)
43 second PM amount estimation unit (estimation means)
44 third PM amount estimation unit (estimation means)
45 total PM amount estimation unit

The invention claimed is:
1. A sensor comprising:
a collection part in which a plurality of filter members, which are for collecting particulate matter in exhaust gas and have different porosities from each other, are arranged in descending order of the porosity from an exhaust upstream side to an exhaust downstream side of the exhaust gas;
a plurality of pairs of electrodes, each pair of the plurality of pairs of electrodes being arranged to one of the plurality of filter members, and the electrodes of each pair of the plurality of pairs of electrodes facing each other such that the one of the plurality of filter members is interposed between the each pair of the plurality of pairs of electrodes; and
an electronic control unit (ECU) which estimates a particulate matter amount collected on each of the plurality of filter members having the different porosities from each other based on a capacitance change amount between the each pair of the plurality of pairs of electrodes;

wherein the ECU estimates a particulate matter amount in the exhaust gas in real time by sequentially adding up the particulate matter amounts collected on the each of the plurality of filter members based on the capacitance change amounts thereof, during a regeneration interval period from an end of a filter regeneration to a start of a next filter regeneration by the ECU.

2. The sensor according to claim 1, further comprising:
the ECU which performs, in a case where the particulate matter amount collected on one of the plurality of filter members becomes equal to or greater than a predetermined amount, the filter regeneration in which the particulate matter is burned and removed by heating the plurality of filter members including at least the one of the plurality of filter members.

3. The sensor according to claim 1,
wherein the each of the plurality of filter members is a filter member including a cell sectioned by a porous partition wall, and
wherein the ECU includes a heating wire which is inserted into the cell and generates heat by being energized.

4. The sensor according to claim 1,
wherein the each of the plurality of filter members is a filter layer in which a plurality of cells are arranged in parallel in one direction, the pair of electrode members comprises first and second electrode plates which are flat and arranged to face each other with the filter layer interposed therebetween, the ECU includes a flat heater substrate which generates heat by being energized, and the flat heater substrate is provided between the first electrode plate and the filter layer or between the second electrode plate and the filter layer.

5. The sensor according to claim 1, wherein the plurality of filter members include a first filter member having a first porosity, and second filter member having a second porosity larger than the first porosity.

6. The sensor according to claim 5, wherein the plurality of pairs of electrodes include a first pair of electrodes facing each other such that the first filter member is interposed between the first pair of electrodes, and a second pair of electrodes facing each other such that the second filter member is interposed between the second pair of electrodes.

7. The sensor according to claim 6, wherein the ECU estimates the particulate matter amount collected on the each of the plurality of filter members based on a capacitance change amount between the first pair of electrodes, and a capacitance change amount between the second pair of electrodes.

8. A sensor comprising:
a collection part in which a plurality of filter members, which are for collecting particulate matter in exhaust gas and have different physical properties from each other, are arranged in descending order of the physical property from an exhaust upstream side to an exhaust downstream side of the exhaust gas;
a plurality of pairs of electrodes, each pair of the plurality of pairs of electrodes being arranged to one of the plurality of filter members, and the electrodes of each pair of the plurality of pairs of electrodes facing each other such that the one of the plurality of filter members interposed between the each pair of the plurality of pairs of electrodes; and
an electronic control unit (ECU),
wherein the physical property is a porosity or an average pore size; and
estimation processing for estimating a particulate matter amount collected on each of the plurality of filter members having the different physical properties based on a capacitance change amount between the each pair of the plurality of pairs of electrodes;
wherein the ECU estimates a particulate matter amount in the exhaust gas in real time by sequentially adding up the particulate matter amounts collected on the each of the plurality of filter members based on the capacitance change amounts thereof, during a regeneration interval period from an end of a filter regeneration to a start of a next filter regeneration by the ECU.

9. The sensor according to claim 8,
wherein the ECU further operates to execute the following processing:
regeneration processing for performing, in a case where the particulate matter amount collected on one of the plurality of filter members becomes equal to or greater than a predetermined amount, the filter regeneration in which the particulate matter is burned and removed by heating the plurality of filter members including at least the one of the plurality of filter members.

10. The sensor according to claim 8, wherein the plurality of filter members include a first filter member having a first porosity, and second filter member having a second porosity larger than the first porosity.

11. The sensor according to claim 10, wherein the plurality of pairs of electrodes include a first pair of electrodes facing each other such that the first filter member is interposed between the first pair of electrodes, and a second pair of electrodes facing each other such that the second filter member is interposed between the second pair of electrodes.

12. The sensor according to claim 11, wherein the ECU estimates the particulate matter amount collected on the each of the plurality of filter members based on a capacitance change amount between the first pair of electrodes, and a capacitance change amount between the second pair of electrodes.

13. A sensor comprising:
a collection part in which a plurality of filter members, which are for collecting particulate matter in exhaust gas and have different average pore sizes from each other, are arranged in descending order of the average pore size from an exhaust upstream side to an exhaust downstream side of the exhaust gas;
a plurality of pairs of electrodes, each pair of the plurality of pairs of electrodes being arranged to one of the plurality of filter members, and the electrodes of each pair of the plurality of pairs of electrodes facing each other such that the one of the plurality of filter members is interposed between the each pair of the plurality of pairs of electrodes; and
an electronic control unit (ECU) which estimates a particulate matter amount collected on each of the plurality of filter members having the different average pore sizes from each other based on a capacitance change amount between the each pair of the plurality of pairs of electrodes;
wherein the ECU estimates a particulate matter amount in the exhaust gas in real time by sequentially adding up the particulate matter amounts collected on the each of the plurality of filter members based on the capacitance change amounts thereof, during a regeneration interval period from an end of a filter regeneration to a start of a next filter regeneration by the ECU.

14. The sensor according to claim 13, further comprising:
the ECU which performs, in a case where the particulate matter amount collected on one of the plurality of filter members becomes equal to or greater than a predetermined amount, the filter regeneration in which the particulate matter is burned and removed by heating the plurality of filter members including at least the one of the plurality of filter members.

15. The sensor according to claim 13,
wherein the each of the plurality of filter members is a filter member including a cell sectioned by a porous partition wall, and
wherein the ECU includes a heating wire which is inserted into the cell and generates heat by being energized.

16. The sensor according to claim 13,
wherein the each of the plurality of filter members is a filter layer in which a plurality of cells are arranged in parallel in one direction, the pair of electrode members comprises first and second electrode plates which are flat and arranged to face each other with the filter layer interposed therebetween, the ECU includes a flat heater substrate which generates heat by being energized, and the flat heater substrate is provided between the first electrode plate and the filter layer or between the second electrode plate and the filter layer.

* * * * *